United States Patent
Kinouchi et al.

(10) Patent No.: US 11,058,285 B2
(45) Date of Patent: Jul. 13, 2021

(54) OPTICAL SIGNAL TRANSMISSION MODULE

(71) Applicant: OLYMPUS CORPORATION, Tokyo (JP)

(72) Inventors: Hideaki Kinouchi, Musashino (JP); Yasuhiro Miyazaki, Hachioji (JP); Tsutomu Urakawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 225 days.

(21) Appl. No.: 16/188,861

(22) Filed: Nov. 13, 2018

(65) Prior Publication Data
US 2020/0022567 A1   Jan. 23, 2020

Related U.S. Application Data

(63) Continuation of application No. PCT/JP2017/008243, filed on Mar. 2, 2017.

(30) Foreign Application Priority Data

May 23, 2016   (JP) .............................. JP2016-102404

(51) Int. Cl.
*A61B 1/00* (2006.01)
*G02B 6/42* (2006.01)
*A61B 1/05* (2006.01)

(52) U.S. Cl.
CPC ...... *A61B 1/00126* (2013.01); *A61B 1/00165* (2013.01); *G02B 6/424* (2013.01);
(Continued)

(58) Field of Classification Search
CPC ............ A61B 1/00126; A61B 1/00165; G02B 6/4206; G02B 6/4239; G02B 6/424; G02B 6/4245
See application file for complete search history.

(56) References Cited

U.S. PATENT DOCUMENTS

| 4,756,591 A | 7/1988 | Fischer et al. |
| 2002/0159719 A1 | 10/2002 | Ide et al. |

(Continued)

FOREIGN PATENT DOCUMENTS

| CN | 104956555 A | 9/2015 |
| EP | 1515364 A2 | 3/2005 |

(Continued)

OTHER PUBLICATIONS

International Search Report dated Jun. 6, 2017 issued in PCT/JP2017/008243.

*Primary Examiner* — Tony Ko
(74) *Attorney, Agent, or Firm* — Scully, Scott, Murphy & Presser, P.C.

(57) ABSTRACT

An optical signal transmission module is provided, in which a lens surface for condensing light emitted from an LD configured to convert an electrical signal to an optical signal and emit light of the optical signal is integrally formed on an end portion of an optical fiber, a mounting substrate for the LD to be mounted is configured with a specially-shaped substrate, and a fixing portion (a fixing hole portion) for the optical fiber to be fixed is integrally formed on the mounting substrate, at a position where the light emitted from the LD (the light of the optical signal) can be incident on the lens surface.

2 Claims, 11 Drawing Sheets

(52) U.S. Cl.
CPC ......... *G02B 6/4206* (2013.01); *G02B 6/4239* (2013.01); *G02B 6/4245* (2013.01); *A61B 1/05* (2013.01)

(56) References Cited

U.S. PATENT DOCUMENTS

| | | |
|---|---|---|
| 2005/0110157 A1 | 5/2005 | Sherrer et al. |
| 2013/0301982 A1* | 11/2013 | Lee .................. G02B 6/423 385/14 |
| 2015/0003484 A1 | 1/2015 | Muendel |
| 2015/0380894 A1 | 12/2015 | Yoshino et al. |
| 2020/0100664 A1* | 4/2020 | Ohno ................... A61B 1/051 |

FOREIGN PATENT DOCUMENTS

| | | |
|---|---|---|
| JP | S56-054081 A | 5/1981 |
| JP | S57013409 A | 1/1982 |
| JP | S60-182404 A | 9/1985 |
| JP | H07104152 A | 4/1995 |
| JP | H08201660 A | 8/1996 |
| JP | H11-160585 A | 6/1999 |
| JP | 2002311305 A | 10/2002 |
| JP | 2003202466 A | 7/2003 |
| JP | 2004317630 A | 11/2004 |
| JP | 2010194037 A | 9/2010 |
| JP | 2012147007 A | 8/2012 |
| JP | 2014-178598 A | 9/2014 |

\* cited by examiner

OPTICAL SIGNAL TRANSMISSION MODULE

CROSS REFERENCE TO RELATED APPLICATION

This application is a continuation application of PCT/JP2017/008243 filed on Mar. 2, 2017 and claims benefit of Japanese Application No. 2016-102404 filed in Japan on May 23, 2016, the entire contents of which are incorporated herein by this reference.

BACKGROUND OF THE INVENTION

Field of the Invention

The present invention relates to an optical signal transmission module for converting an electrical signal to an optical signal and transmitting the optical signal.

Description of the Related Art

Conventionally, among endoscopes, an electronic endoscope provided with an image pickup device such as a CCD on a distal end portion of an elongated insertion portion having flexibility has been widely spread. Recently, increase in the number of pixels of the image pickup device has been promoted for the type of endoscope.

If the number of pixels of the image pickup device is increased, a signal amount transmitted from the image pickup device to a signal processing apparatus (a processor) increases. In this case, it is preferable that transmission of an image pickup signal acquired by the image pickup device is performed by optical signal transmission via a thin optical fiber instead of electrical signal transmission via metal wiring.

In order to perform such optical signal transmission, an optical signal transmission module generally includes a light emitting device such as a laser diode (LD) as a light source for converting an electrical signal to an optical signal, and a main part is configured by an end portion of an optical fiber held by a ferrule or the like being optically connected to the light emitting device.

As a configuration for optically connecting a light emitting device and an optical fiber, for example, Japanese Patent Application Laid-Open Publication No. 2010-194037 discloses a connecting portion provided with a plate-shaped optical waveguide configured to transmit an optical signal from an LD and a guide block configured to fix an end portion of the optical fiber connected to the optical waveguide.

SUMMARY OF THE INVENTION

An optical signal transmission module according to an aspect of the present invention is an optical signal transmission module including: a light emitting device configured to convert an electrical signal to an optical signal and emit light of the optical signal; an optical fiber configured to transmit the optical signal caused to be incident via a light condensing portion for condensing the light emitted from the light emitting device, the light condensing portion being integrally formed on an end portion of the optical fiber; and a mounting substrate configured with a specially-shaped substrate on which a mounting portion for the light emitting device to be mounted and a fixing portion for the optical fiber to be fixed at a position where the light emitted from the light emitting device mounted on the mounting portion is caused to be incident on the light condensing portion are integrally formed, wherein the fixing portion includes a fixing hole portion configured to fix a distal end of the optical fiber such that the distal end is insertable on a same axis; the mounting portion includes a terminal portion configured to electrically mount the light emitting device so that positioning of the light emitting device is possible in a plane vertical to a direction of the axis; and, in the mounting substrate, a through hole is integrally formed, the through hole being formed thinner than an outer diameter of the optical fiber, coaxially communicating with the fixing hole portion, and penetrating to the mounting portion side; an optical axis of the light emitting device is coaxial with a central axis of the optical fiber; and the light emitting device is mounted on the mounting portion with the terminal portion as a positioning reference.

An optical signal transmission module according to another aspect of the present invention is an optical signal transmission module including: a plurality of light emitting devices each configured to convert an electrical signal to an optical signal and emit light of the optical signal; an optical fiber configured to transmit the optical signal caused to be incident via a light condensing portion for condensing the light emitted from each of the light emitting devices, the light condensing portion being integrally formed on an end portion of the optical fiber; and a mounting substrate configured with a specially-shaped substrate on which mounting portions for the plurality of light emitting devices to be mounted and a fixing portion for the optical fiber to be fixed at a position where the light emitted from each of the light emitting devices mounted on the mounting portions are caused to be incident on the light condensing portion are integrally formed, wherein the fixing portion includes a fixing hole portion configured to fix a distal end of the optical fiber such that the distal end is insertable on a same axis; and, on the mounting substrate, the mounting portions are set on a bottom portion of the fixing hole portion, and the plurality of light emitting devices are mounted on the mounting portions.

An optical signal transmission module according to another aspect of the present invention is an optical signal transmission module including: a plurality of light emitting devices each configured to convert an electrical signal to an optical signal and emit light of the optical signal; an optical fiber configured to transmit the optical signal caused to be incident via a light condensing portion for condensing the light emitted from each of the light emitting devices, the light condensing portion being integrally formed on an end portion of the optical fiber; and a mounting substrate configured with a specially-shaped substrate on which mounting portions for the plurality of light emitting devices to be mounted and a fixing portion for the optical fiber to be fixed at a position where the light emitted from each of the light emitting devices mounted on the mounting portions are caused to be incident on the light condensing portion are integrally formed, wherein the fixing portion includes a fixing groove portion for fixing a side face on a distal end side of the optical fiber, the fixing groove portion forming a partial arc shape; and, on the mounting substrate, a plurality of the mounting portions are arranged on a plane orthogonal to a central axis of the optical fiber.

DETAILED DESCRIPTION OF THE PREFERRED EMBODIMENT(S)

Figure 1:
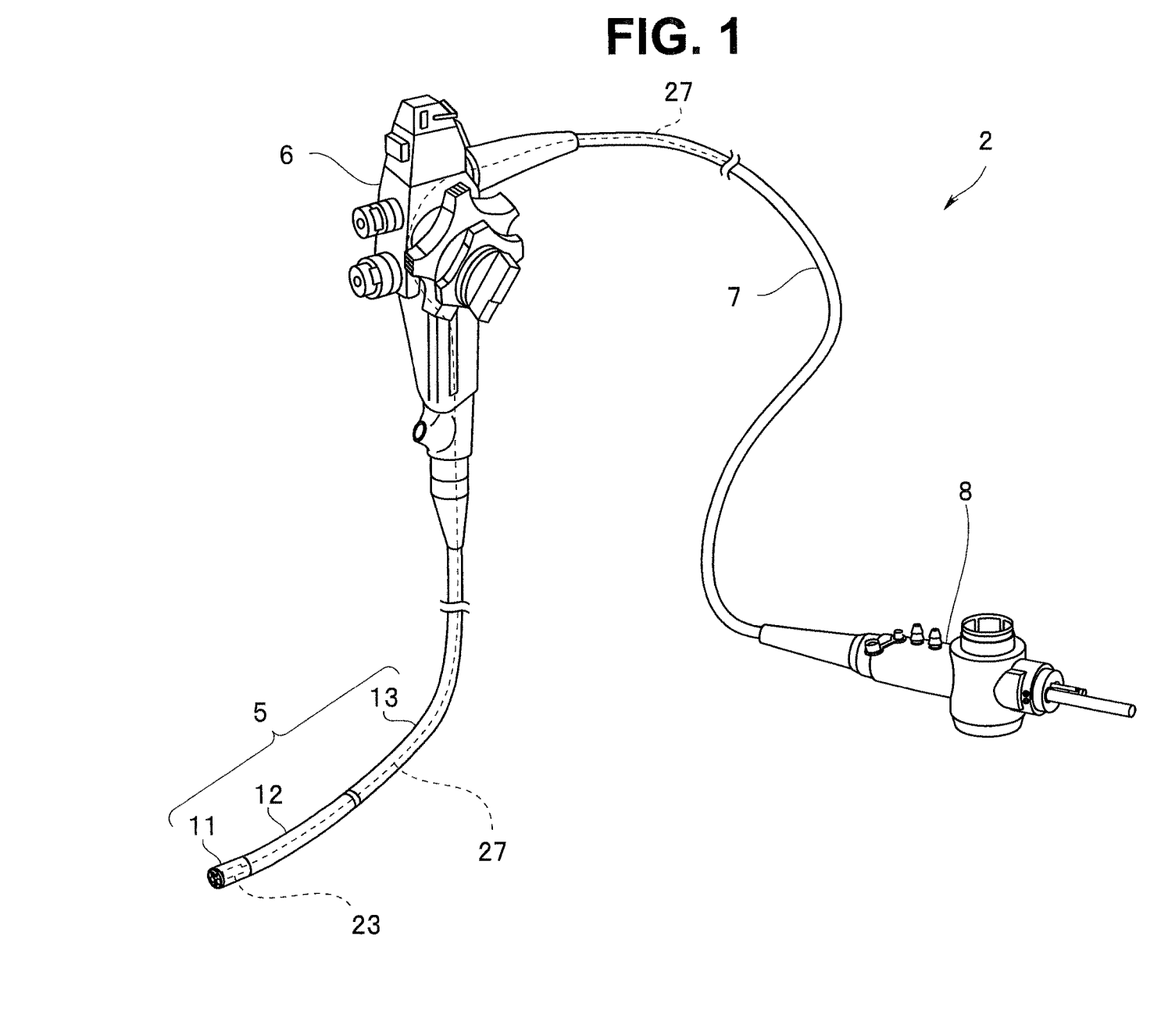
FIG. 1 relates to a first embodiment of the present invention and is a perspective view of an endoscope.
Figure 2:
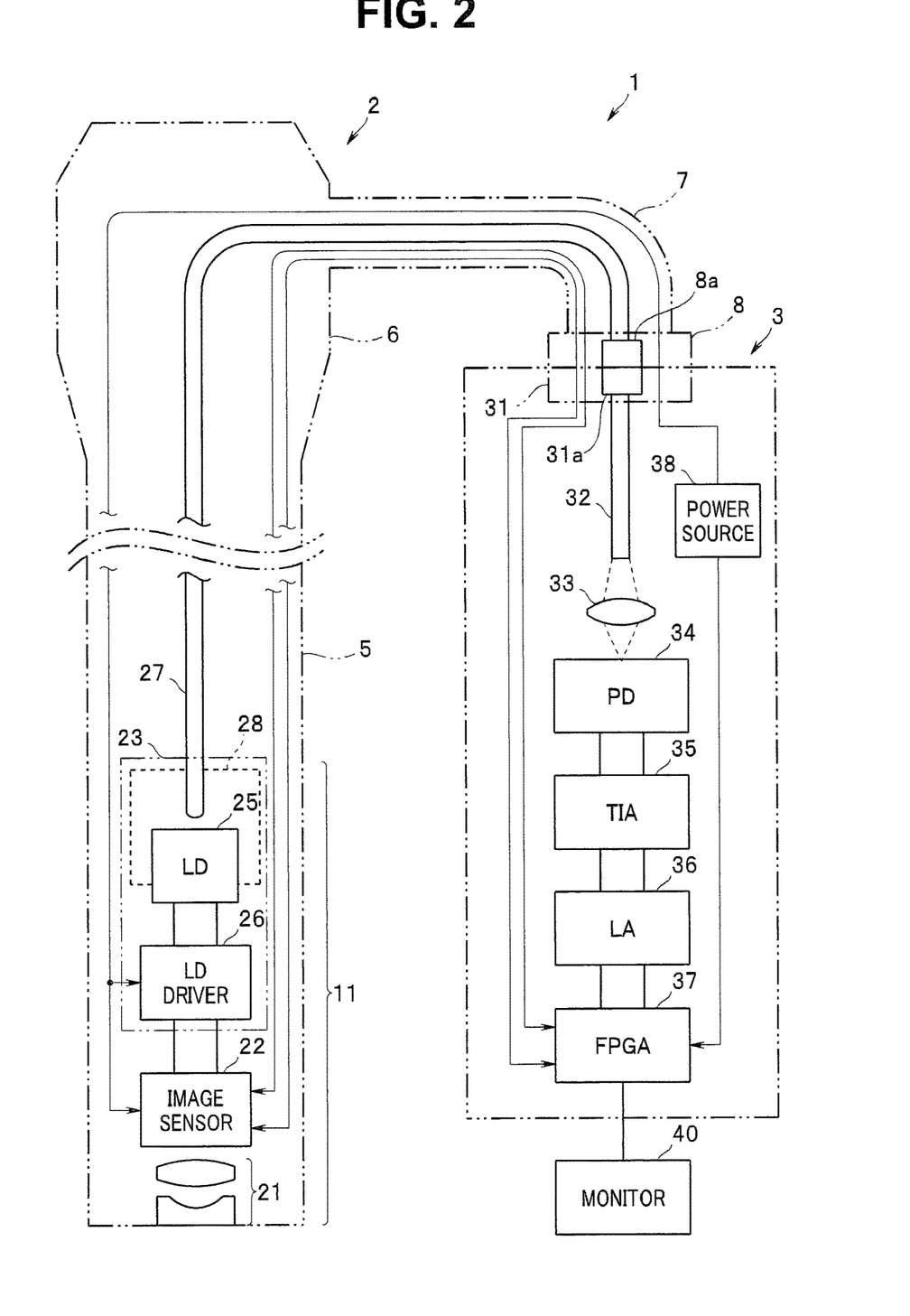
FIG. 2 relates to the first embodiment of the present invention and is a functional block diagram showing a video signal transmission system in an endoscope system.
Figure 3:
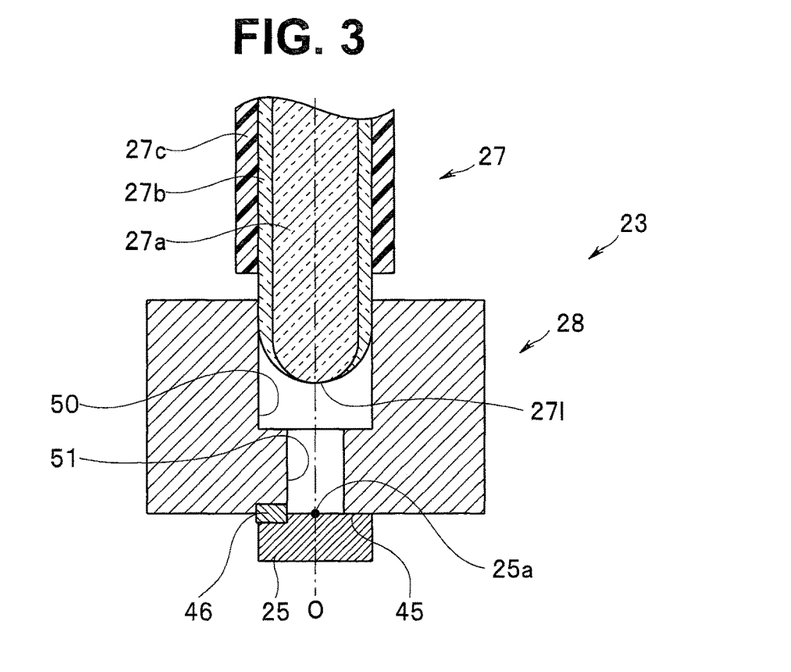
FIG. 3 relates to the first embodiment of the present invention and is a cross-sectional view of a main part of an optical signal transmission module.
Figure 4:
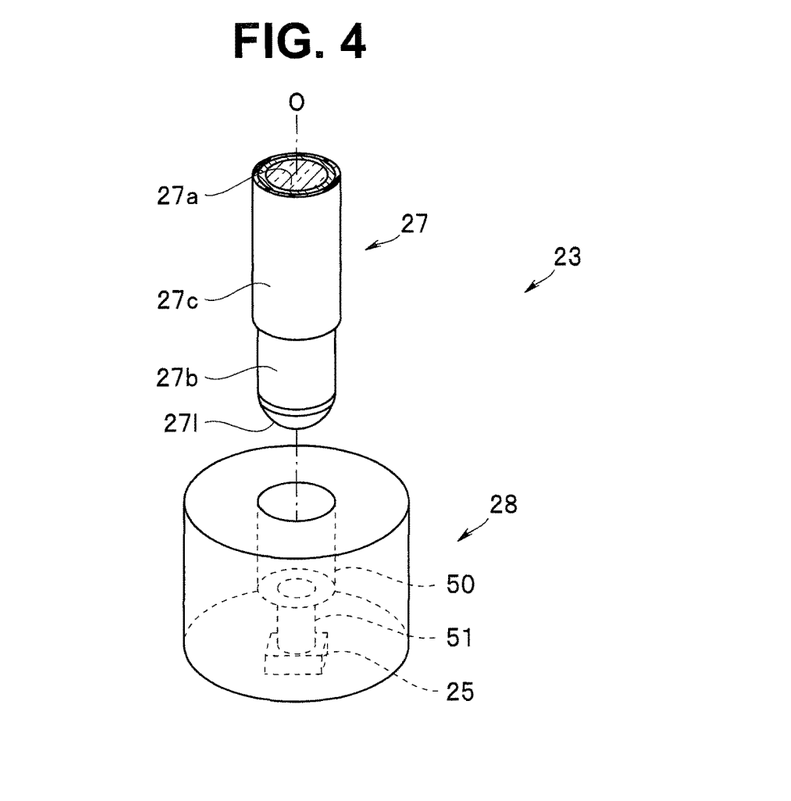
FIG. 4 relates to the first embodiment of the present invention and is an exploded perspective view showing the main part of the optical signal transmission module.

Embodiments of the present invention will be described below with reference to drawings. FIGS. 1 to 4 relate to a first embodiment of the present invention. FIG. 1 is a perspective view of an endoscope; FIG. 2 is a functional block diagram showing a video signal transmission system in an endoscope system; FIG. 3 is a cross-sectional view of a main part of an optical signal transmission module; and FIG. 4 is an exploded perspective view showing the main part of the optical signal transmission module.

An endoscope 2 shown in FIG. 1 is configured including an insertion portion 5, an operation portion 6 disposed on a proximal end side of the insertion portion 5, a universal cord 7 extending from the operation portion 6 and a connector 8 disposed on a proximal end side of the universal cord 7.

The insertion portion 5 is configured with a rigid distal end portion 11, a bending portion 12 for causing a direction of the distal end portion 11 to change, a flexible tube portion 13, which is elongated and flexible, being connected in the order from a distal end side.

As shown in FIG. 2, in the distal end portion 11, an image pickup optical unit 21, an image sensor 22 configured to pick up an optical image formed by the image pickup optical unit 21, and an optical signal transmission module 23 which is an E/O module configured to convert an image pickup signal (an electrical signal) from the image sensor 22 to an optical signal are arranged.

The image sensor 22 is configured with a solid-state image pickup device such as a CMOS (complementary metal oxide semiconductor) or a CCS (charge coupled device).

The optical signal transmission module 23 is configured including a surface-emission-type laser diode (LD) 25 as a light emitting device, an LD driver 26 configured to perform driving control of the LD 25 based on an image pickup signal from the image sensor 22 to cause an optical signal to be emitted from the LD 25, an optical fiber 27 for transmitting the optical signal emitted from the LD 25, and a mounting substrate 28 on which the LD 25 is mounted, and the optical fiber 27 is held.

Here, the optical fiber 27 is configured, for example, with a multi-mode fiber (MMF). One end side of the optical fiber 27 is inserted in the universal cord 7 via the operation portion 6 and can be connected to a processor 3 via a receptacle 8a of an optical connector provided on the connector 8.

As shown in FIG. 2, the processor 3 is for constituting an endoscope system 1 together with the endoscope 2 and includes a connector 31 which the connector 8 of the endoscope 2 can be freely attached to and detached from, and an optical fiber 32 which is optically connected to the optical fiber 27 (the receptacle 8a) via a plug 31a of an optical connector provided on the connector 31.

Furthermore, the processor 3 includes: a collimator 33 for condensing an optical signal transmitted from the optical fiber 27 to the optical fiber 32, a photodiode (PD) 34 configured to photoelectrically convert the optical signal condensed by the collimator 33, a trans-impedance amplifier (TIA) 35 configured to perform impedance conversion of a current signal photoelectrically converted by the PD 34 to amplify the signal, and output the signal as a voltage signal, a limiting amplifier (LA) 36 configured to cause an amplitude of the voltage signal amplified by the TIA 35 to be constant, and a field programmable gate array (FPGA) 37 as an image pickup controlling portion configured to output a clock signal or a control signal to the image sensor 22 and the like via a signal line and process the voltage signal from the LA 36 to display an object image on a monitor 40.

Note that the processor 3 includes a power source circuit 38, and the power source circuit 38 can supply driving power and the like to each portion of the endoscope 2 and the processor 3 via electrical wiring.

Next, a structure of holding the optical fiber 27 in the optical signal transmission module 23 will be described with reference to FIGS. 3 and 4.

In the present embodiment, the optical fiber 27 is held by a fixing portion integrally formed on the mounting substrate 28 for the LD 25 to be mounted.

More specifically, the mounting substrate 28 of the present embodiment is configured with a specially-shaped substrate (that is, a substrate which is not flat) which forms an almost cylindrical shape following an internal space in the distal end portion 11.

At a central part on a distal end surface (one end surface) of the mounting substrate 28, a mounting portion 45 for the LD 25 to be mounted is set. The mounting portion 45 is provided with a plurality of terminal portions 46 at positions slightly offset from a center of the mounting substrate 28, and the LD 25 is mounted on the mounting portion 45 of the mounting substrate 28 by being electrically connected to each of the terminal portions 46. That is, the LD 25 of the present embodiment is configured with a so-called flip chip type back-surface radiation laser (a surface light emission laser) which is provided with a light emitting portion 25a on a back side surface which is in contact with the mounting substrate 28. By respective bumps provided on the LD 25 being electrically connected to the respective terminal portions 46, respectively, the LD 25 is mounted on the mounting substrate 28.

At a center on a proximal end side of the mounting substrate 28, a fixing hole portion 50 as a fixing portion into which a distal end of the optical fiber 27 can be inserted is provided. Here, for the optical fiber 27 of the present embodiment, for example, a diameter of a core 27a is 50 μm, and a diameter including a clad 27b provided on an outer circumference of the core 27a is 80 μm. According to such dimensions, the fixing hole portion 50 the diameter of which is about 80 μm is formed in the mounting substrate 28.

In a bottom portion of the fixing hole portion 50, a through hole 51 penetrating to a distal end surface side of the mounting substrate 28 is provided. The light emitting portion 25a of the LD 25 mounted on the mounting substrate 28 is caused to face the through hole 51. More specifically, the through hole 51 of the present embodiment is provided coaxially with the fixing hole portion 50, and the LD 25 is mounted on the mounting substrate 28 such that an optical axis O of the light emitting portion 25a is located coaxially with the through hole 51 and the fixing hole portion 50.

Relative to the mounting substrate 28 as described above, the distal end of the optical fiber 27 is inserted in the fixing hole portion 50 and fixed by an inserted part being caused to adhere via adhesive or the like. By the optical fiber 27 being fixed to the mounting substrate 28 as described above, a distal end surface of the optical fiber 27 is accurately fixed to a position facing the light emitting portion 25a of the LD 25.

Here, as the optical fiber 27 of the present embodiment, an optical fiber the numerical aperture NA of which is within a range of 0.2 to 0.3 is used, the numerical aperture NA indicating the magnitude of a maximum acceptance angle. In order to cause a laser beam radiated from the light emitting portion 25a to be efficiently condensed and incident on the optical fiber 27 with such a numerical aperture, a lens surface 271 formed by a predetermined curved surface is integrally formed on the distal end surface of the optical fiber 27 as a light condensing portion by processing using etching or the like.

In this case, for example, a partial spherical surface within a range of R=1600 to R=3 can be adopted as the lens surface 271. In the present embodiment, the lens surface 271 is formed by a partial spherical surface with R=100 μm. Note that it is desirable that reflective coating is applied to the lens surface 271.

According to such an embodiment, by integrally forming the lens surface 271 for condensing light emitted from the LD 25 configured to convert an electrical signal to an optical signal and emit light of the optical signal, on an end portion of the optical fiber 27, configuring the mounting substrate 28 for the LD 25 to be mounted with a specially-shaped substrate, and integrally forming a fixing portion (the fixing hole portion 50) for an optical fiber to be fixed at a position where light emitted from the LD 25 (light of an optical signal) can be caused to be incident on the lens surface 271, on the mounting substrate 28, it is possible to, by a simple configuration, cause the optical signal emitted from the LD 25 to be appropriately incident on the optical fiber 27.

That is, by configuring the mounting substrate 28 with a specially-shaped substrate and integrally forming the fixing hole portion 50 for fixing the optical fiber 27 on the mounting substrate 28, it is possible to optically connect the LD 25 and the optical fiber 27 by a simple configuration without separately using a dedicated part such as a ferrule. In addition, by integrally forming the lens surface 271 on the distal end of the optical fiber 27, it is possible to cause most of an optical signal emitted from the LD 25 to be appropriately incident on the optical fiber 27 by a simple configuration without causing an optical device or the like to intervene between the LD 25 and the optical fiber 27. Therefore, it is possible to suppress increase in a rigid length of the distal end portion 11 of the endoscope 2.

Moreover, by integrally forming the fixing hole portion 50 in the mounting substrate 28, it is unnecessary to perform positioning between the fixing hole portion 50 and the mounting substrate 28 at the time of assembling and the like, and it is possible to accurately and easily realize optical connection between the LD 25 and the optical fiber 27 only by accurately positioning the LD 25 relative to the mounting substrate 28.

Figure 5:
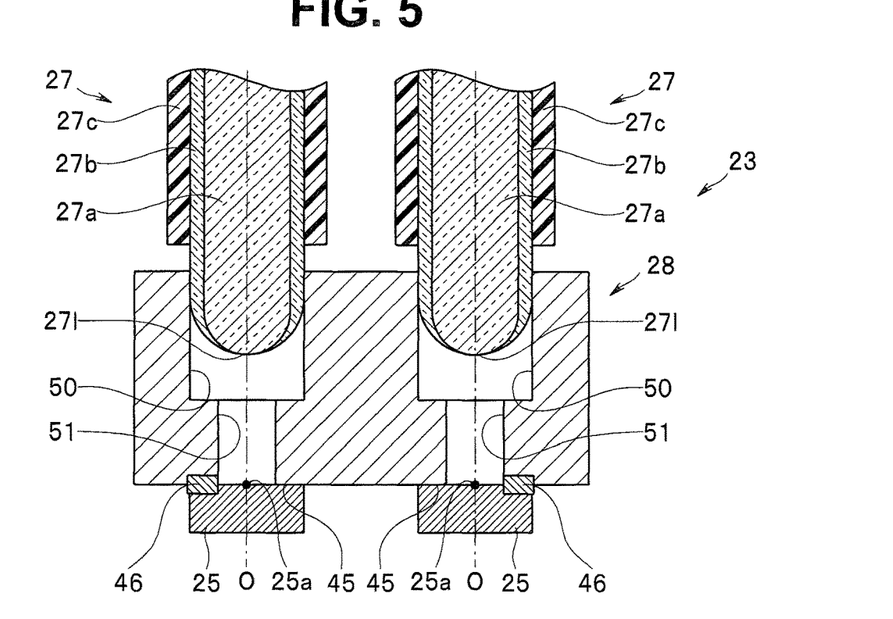
FIG. 5 relates to a first modification of the first embodiment of the present invention and is a cross-sectional view of a main part of an optical signal transmission module.
Figure 6:
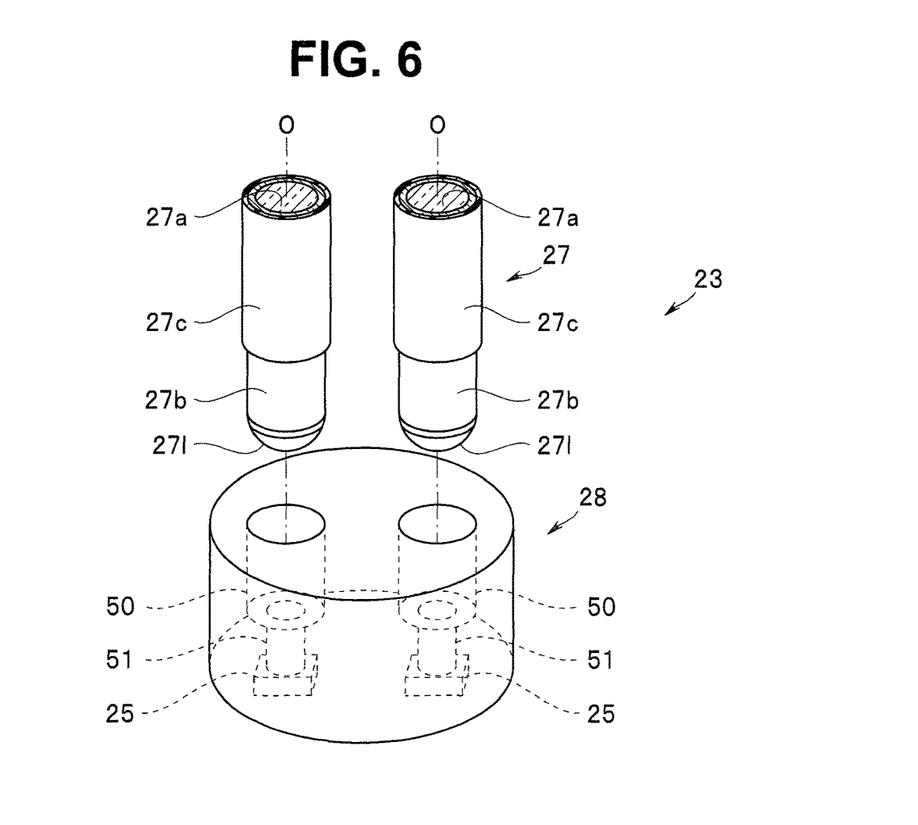
FIG. 6 relates to the first modification of the first embodiment of the present invention and is an exploded perspective view showing the main part of the optical signal transmission module.

Here, for example, as shown in FIGS. 5 and 6, it is also possible to provide two sets of the mounting portion 45, the fixing hole portion 50 and the through hole 51 relative to the mounting substrate 28, and optically connect each LD 25 to each separate optical fiber 27. By making such a configuration, more image pickup signals and the like can be transmitted.

Figure 7:
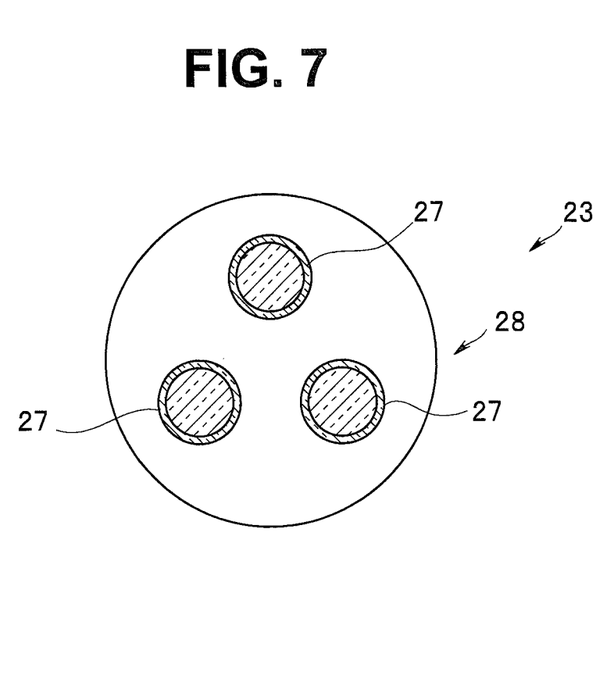
FIG. 7 relates to a second modification of the first embodiment of the present invention and is an end view showing an optical signal transmission module from a proximal end side.
Figure 8:
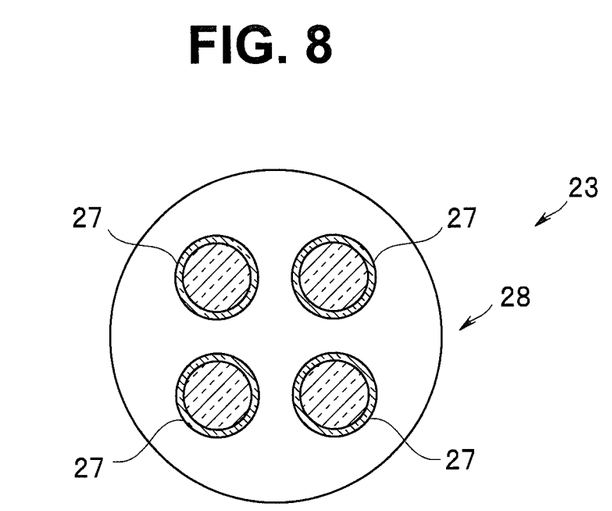
FIG. 8 relates to a third modification of the first embodiment of the present invention and is an end view showing an optical signal transmission module from a proximal end side.

Furthermore, for example, as shown in FIGS. 7 and 8, it is also possible to fix three or four optical fibers 27 associated with LDs 25, respectively, relative to the mounting substrate 28, and it is also possible to fix five or more optical fibers 27 by a configuration similarly to the above, although it is not shown.

Figure 9:
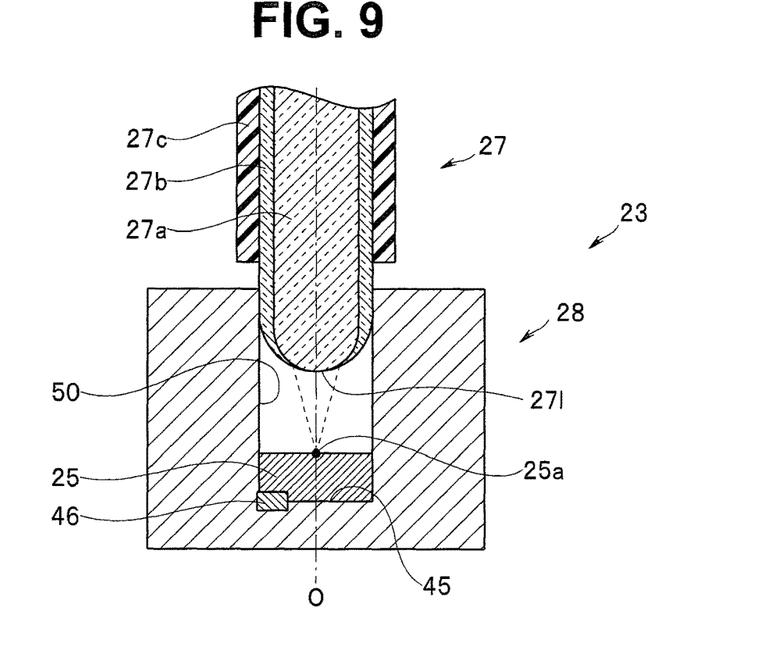
FIG. 9 relates to a fourth modification of the first embodiment of the present invention and is a cross-sectional view of a main part of an optical signal transmission module.
Figure 10:
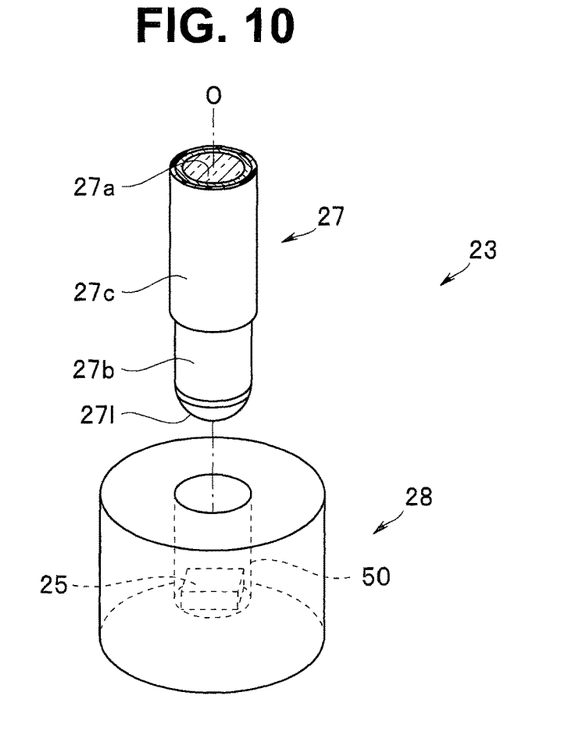
FIG. 10 relates to the fourth modification of the first embodiment of the present invention and is an exploded perspective view showing the main part of the optical signal transmission module.

For example, as shown in FIGS. 9 and 10, it is also possible to remove the through hole 51 and provide the mounting portion 45 and the terminal portions 46 on an end surface of the fixing hole portion 50. Note that even in such a configuration, it is also possible to optically connect two or more LDs 25 and two or more optical fibers 27, respectively, by the mounting substrate 28, although it is not shown.

Figure 11:
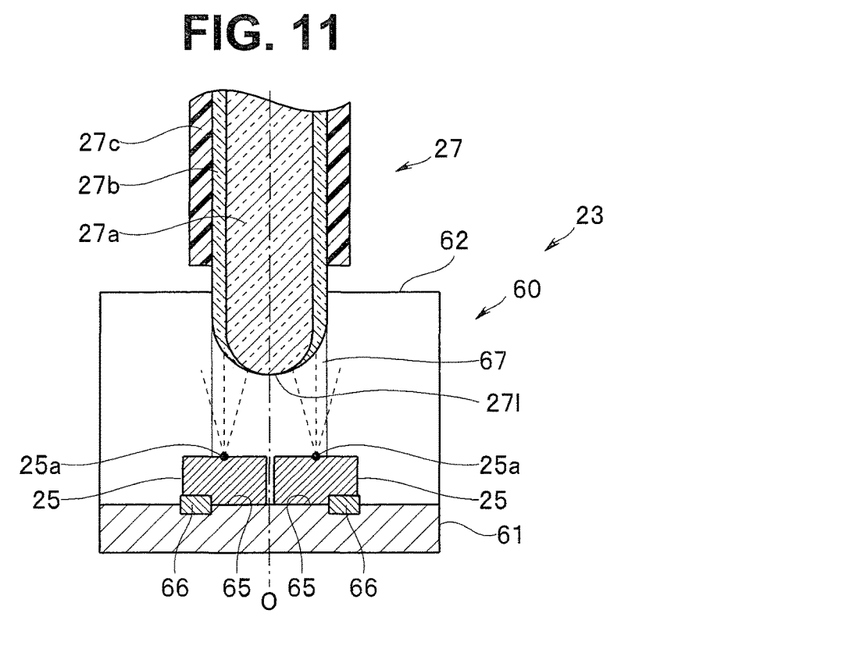
FIG. 11 relates to a second embodiment of the present invention and is a cross-sectional view of a main part of an optical signal transmission module.
Figure 12:
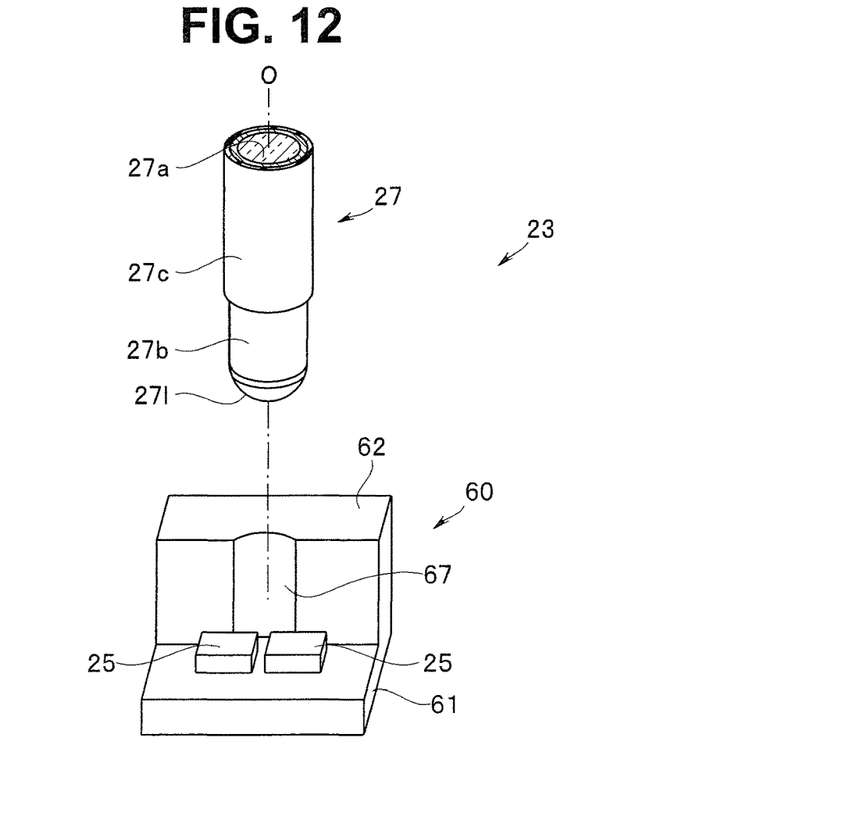
FIG. 12 relates to the second embodiment of the present invention and is an exploded perspective view showing the main part of the optical signal transmission module.
Figure 13:
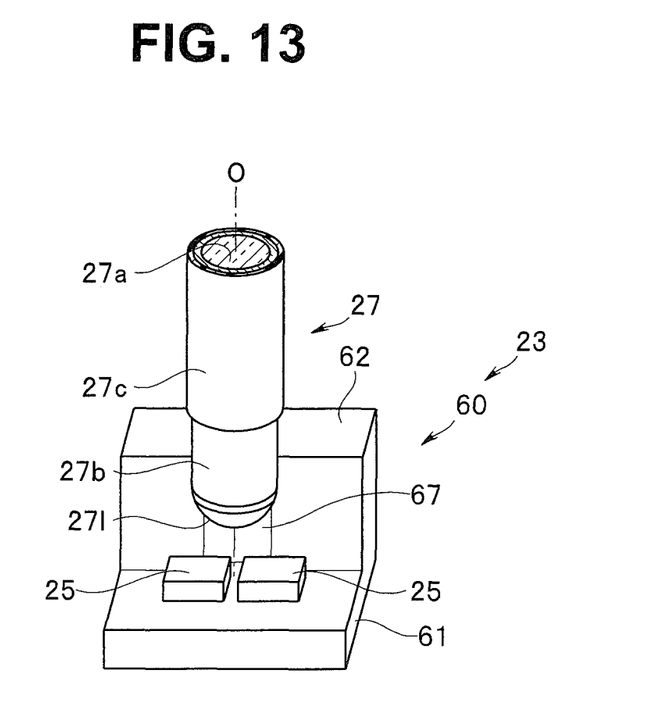
FIG. 13 relates to the second embodiment of the present invention and is a perspective view showing the main part of the optical signal transmission module.
Figure 14:
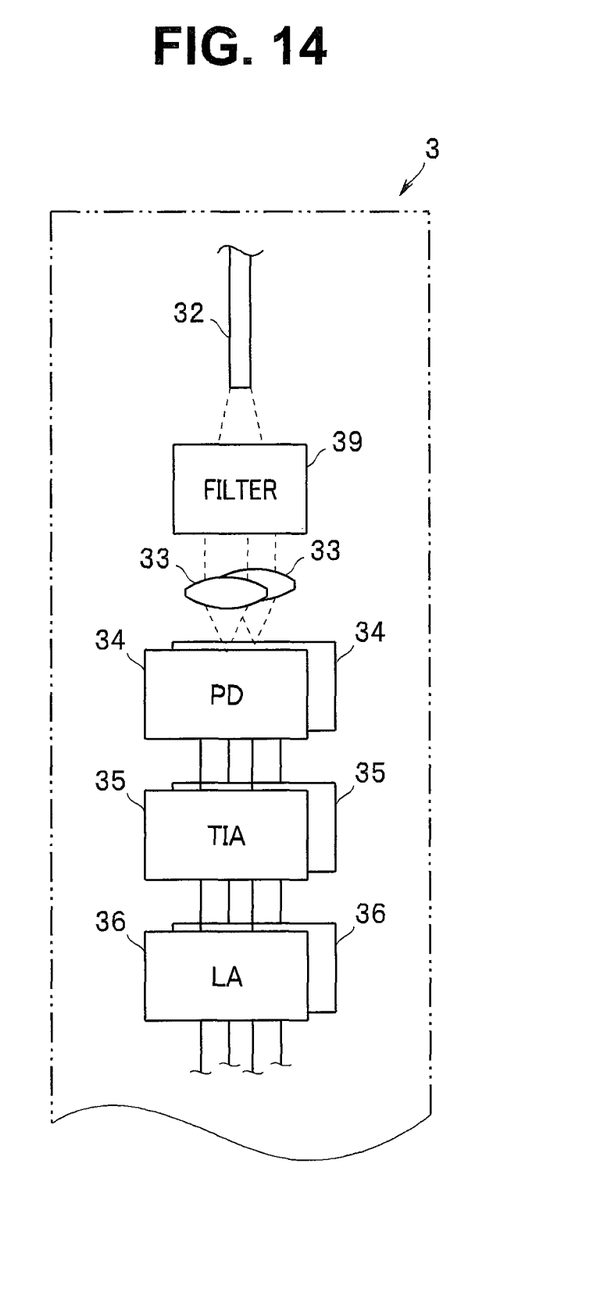
FIG. 14 relates to the second embodiment of the present invention and is a functional block diagram showing a main part of a processor.

Next, FIGS. 11 to 14 relate to a second embodiment of the present invention. FIG. 11 is a cross-sectional view of a main part of an optical signal transmission module; FIG. 12 is an exploded perspective view showing the main part of the optical signal transmission module; FIG. 13 is a perspective view showing the main part of the optical signal transmission module; and FIG. 14 is a functional block diagram showing a main part of a processor. Note that the present embodiment is different from the first embodiment described above mainly in that lights emitted from a plurality of LDs 25 are caused to be incident on one optical fiber 27. Components similar to components of the first embodiment are given the same reference numerals, and description will be appropriately omitted.

As shown in FIGS. 11 to 13, a mounting substrate 60 of the present embodiment is configured with a specially-shaped substrate on which a substrate body 61 in a flat plate shape and a projecting portion 62 extending from the substrate body 61 toward a proximal end side of the distal end portion 11 are integrally formed, a side face of the specially-shaped substrate forming a substantial L shape.

On the substrate body 61, mounting portions 65 for two LDs 25 to be mounted, respectively, are set side by side on a surface where the projecting portion 62 is provided (a proximal end surface). The mounting portions 65 are provided with terminal portions 66, respectively, and the LDs 25 are mounted on the mounting portions 65 of the substrate body 61, respectively, by being electrically connected to the terminal portions 66, respectively. That is, the LD 25 of the present embodiment is configured with a so-called flip chip type front-surface radiation laser (a surface light emission laser) which is provided with the light emitting portion 25a on a front side surface which is not in contact with the substrate body 61. By bumps provided on the LDs 25 being electrically connected to the terminal portions 66, respectively, the LDs 25 are mounted on the mounting substrate 60.

The projecting portion 62 is provided with a fixing groove portion 67 as a fixing portion, with which a side face on a distal end side of the optical fiber 27 can be in contact, on a surface which each LD 25 is cause to face.

The fixing groove portion 67 of the present embodiment is configured with a groove portion forming a partial arc shape with almost the same diameter as the diameter of the clad 27b of the optical fiber 27. The fixing groove portion 67 fixes the side face on the distal end side of the optical fiber 27 by adhesion, and the fixing groove portion 67 is set so that a central axis O of the fixed optical fiber 27 is located between the two LDs 25.

Note that for fixation of the optical fiber 27, adhesive the refractive index of which matches the refractive index of the optical fiber 27 (refractive index matching adhesive) can be preferably used. It is also possible to fill a portion between the optical fiber 27 and the LDs 25 with the refractive index matching adhesive, although it is not shown.

Thereby, each of optical signals emitted from the two LDs 25 is caused to be incident on the optical fiber 27 via the lens surface 271.

Here, in order to prevent the optical signals from the respective LDs 25 from optically interfering with each other, wavelengths of light sources (laser beams) emitted from the respective LDs 25 are set to different wavelengths. In this case, for the wavelengths of the laser beams emitted from the respective LDs 25, it is desirable to provide a certain wavelength interval. Therefore, in the present embodiment, for example, a VCSEL (vertical cavity surface emitting laser) with a wavelength of about 1310 nm is adopted for one LD 25, and a VCSEL with a wavelength of about 1550 nm is adopted for the other LD 25.

Further, in order to appropriately receive and process the optical signals from the two LDs 25, for example, the processor 3 is provided with two systems of the collimator 33, the PD 34, the TIA 35 and the LA 36. Furthermore, between the optical fiber 32 and each of the collimators 33, a filter 39 for separating a laser beam between the laser beams with different wavelengths and causing the laser beam to be incident on each of the collimators 33 intervenes as shown in FIG. 14.

According to such an embodiment, in addition to effects similar to the effects of the embodiment described above, it is possible to transmit optical signals from a plurality of LDs 25 by a single optical fiber 27.

Figure 15:
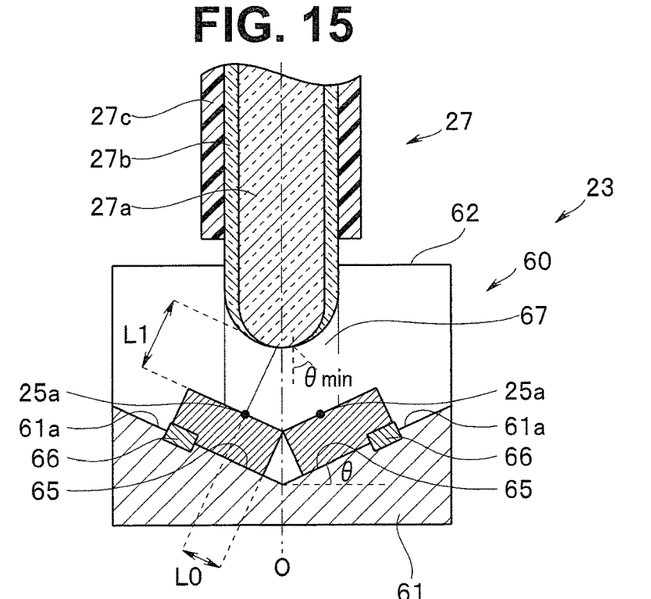
FIG. 15 relates to a first modification of the second embodiment of the present invention and is a cross-sectional view of a main part of an optical signal transmission module.
Figure 16:
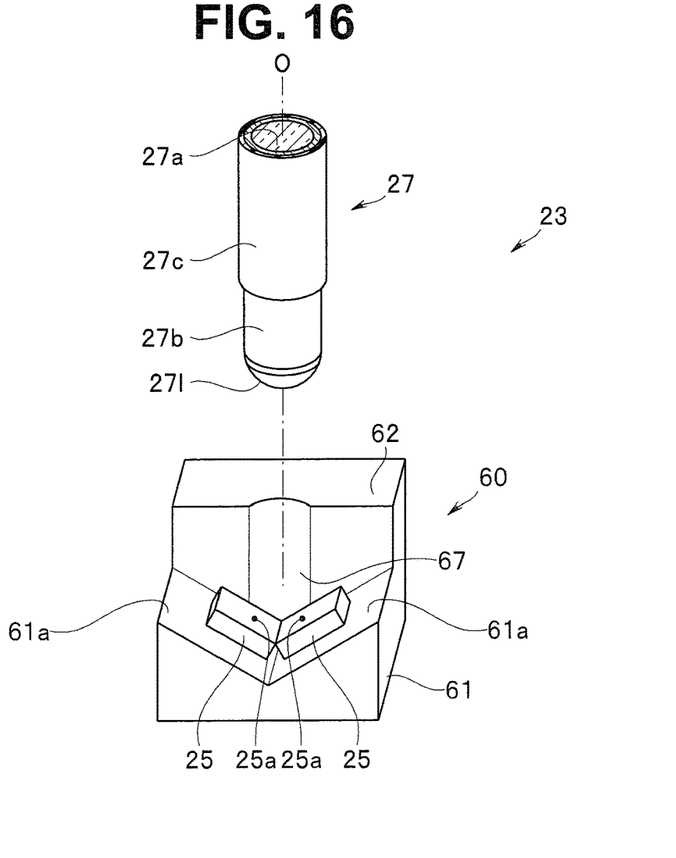
FIG. 16 relates to the first modification of the second embodiment of the present invention and is an exploded perspective view showing the main part of the optical signal transmission module.
Figure 17:
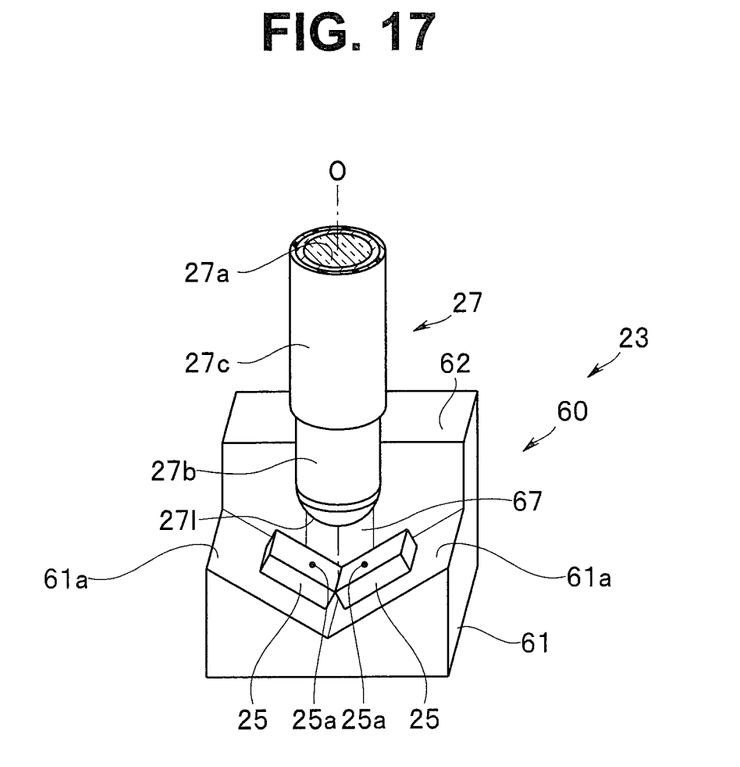
FIG. 17 relates to the first modification of the second embodiment of the present invention and is a perspective view showing the main part of the optical signal transmission module.

Here, in order to cause more optical signals to be incident on the optical fiber 27 from the respective LDs 25, it is possible to, for example, as shown in FIGS. 15 to 17, form inclined surfaces 61a on the substrate body 61, the sections of the inclined surfaces 61a being symmetrical relative to the central axis O of the optical fiber 27 and forming a substantial V shape, and set the mounting portions 65 of the LDs 25 on the inclined surfaces 61a, respectively.

In this case, for example, as shown in FIG. 14, in the case of using such an optical fiber 27 that as for numerical data, a diameter of the fiber core 27a is 50 μm, the maximum numerical aperture NA is 0.27, and θ min=15.67 deg is set, and using such LDs 25 that as for numerical data, the opening of the light emitting portion 25a is 20 μm, it is possible to set the angle θ of the inclined surface 61a to 15.67 deg relative to a surface vertical to the optical axis O, set an amount of offset L0 from the optical axis O of the light emitting portion 25a to 106 μm, and set a distance L1 from the light emitting portion 25a to the lens surface 271 of the optical fiber 27 to 377.9 μm.

Note that the present invention is not limited to each of the embodiments described above, but various modifications and alterations are possible. The modifications and alterations are also within the technical scope of the present invention.

For example, although an example using an MMF as an optical fiber has been described in each of the embodiments described above, the present invention is not limited to the MMF. For example, it is also possible to use a grated index (GI) type MMF, a step index (SI) type MMF or a single mode fiber (SMF).

In the second embodiment described above, instead of the video signal transmission system provided with a filter configured to selectively separate a wavelength, a video signal transmission system can be configured using a 1×2 dichroic optical coupler or the like as demultiplexing means utilizing a wavelength difference.

What is claimed is:

1. An optical signal transmission module comprising:
  a light emitting device configured to convert an electrical signal to an optical signal and emit light of the optical signal on an optical axis;
  an optical fiber configured to transmit the optical signal caused to be incident via a light condensing portion for condensing the light emitted from the light emitting device, the light condensing portion being integrally formed on an end portion of the optical fiber, the optical fiber being extended along a central axis; and
  a mounting substrate configured with a specially-shaped substrate on which a mounting portion for the light emitting device to be mounted and a fixing portion for the optical fiber to be fixed at a position where the light emitted from the light emitting device mounted on the mounting portion is caused to be incident on the light condensing portion are integrally formed, wherein
  the fixing portion includes a fixing hole configured to fix a distal end of the optical fiber such that the central axis at the distal end of the optical fiber is inserted to align with the optical axis of the light emitting device;

the mounting portion includes a terminal portion configured to electrically mount the light emitting device so that positioning of the light emitting device is possible in a plane vertical to a direction of the axis; and in the mounting substrate, a through hole is integrally formed, the through hole being formed thinner than an outer diameter of the optical fiber, coaxially communicating with the fixing hole, and penetrating to the mounting portion side; the optical axis of the light emitting device is coaxial with the central axis of the optical fiber; and the light emitting device is mounted on the mounting portion with the terminal portion as a positioning reference.

2. The optical signal transmission module according to claim 1, wherein in the mounting substrate, at least a partial space is filled with refractive index matching adhesive in a space surrounding the fixing hole portion and the through hole, the space being from the light emitting device to the distal end of the optical fiber.

\* \* \* \* \*